United States Patent
Velez Wiesner

(10) Patent No.: US 11,351,020 B2
(45) Date of Patent: *Jun. 7, 2022

(54) EXTERNAL MALE INCONTINENCE CLAMP

(71) Applicant: Juan Felipe Velez Wiesner, Medellin (CO)

(72) Inventor: Juan Felipe Velez Wiesner, Medellin (CO)

(73) Assignee: WIESNER HEALTHCARE INNOVATION LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/305,844

(22) Filed: Jul. 15, 2021

(65) Prior Publication Data

US 2021/0338404 A1 Nov. 4, 2021

Related U.S. Application Data

(63) Continuation of application No. 16/810,148, filed on Mar. 5, 2020, which is a continuation of application No. 15/253,051, filed on Aug. 31, 2016, now Pat. No. 10,624,728.

(51) Int. Cl.
*A61F 2/00* (2006.01)

(52) U.S. Cl.
CPC .... *A61F 2/0054* (2013.01); *A61F 2220/0091* (2013.01)

(58) Field of Classification Search
CPC ........ A61F 2/00; A61F 2/0004; A61F 2/0009; A61F 2/0013; A61F 2/0018; A61F 2/0031; A61F 2/0054; A61F 2220/0091; Y10S 128/25; A61B 17/122; A61B 17/1322

USPC ......... 128/885, DIG. 25, 842; 606/157, 151, 606/201; 600/29; D24/143

See application file for complete search history.

(56) References Cited

U.S. PATENT DOCUMENTS

| | | | | |
|---|---|---|---|---|
| 3,203,421 | A * | 8/1965 | Bialick | A61F 2/0054 24/514 |
| 5,571,125 | A * | 11/1996 | Chadwick | A61F 2/0054 606/157 |
| 5,842,968 | A * | 12/1998 | Johnson | A61F 5/41 600/38 |
| 2004/0129277 | A1* | 7/2004 | Parkes | A61F 2/0054 128/885 |
| 2014/0041672 | A1* | 2/2014 | Garc a Berruezo | A61F 2/0054 128/885 |
| 2020/0197146 | A1* | 6/2020 | Velez Wiesner | A61F 2/0054 |

* cited by examiner

*Primary Examiner* — Caitlin A Carreiro
(74) *Attorney, Agent, or Firm* — Dunlap Bennett & Ludwig, PLLC; Brendan E. Squire

(57) ABSTRACT

An incontinence clamp is provided. The incontinence clamp includes an upper clamp arm and a lower clamp arm. Each of the upper and lower clamp arms include a first end, a second end, an inner surface and an outer surface. The inner surfaces face each other. A hinge pivotally connects the first ends of the upper and lower clamp arms together. An upper guide is coupled to the inner surface of the upper clamp arm and a lower guide is coupled to the inner surface of the lower clamp arm. A connector releasably connects the second ends of the upper clamp arm and the lower clamp arm together.

16 Claims, 4 Drawing Sheets

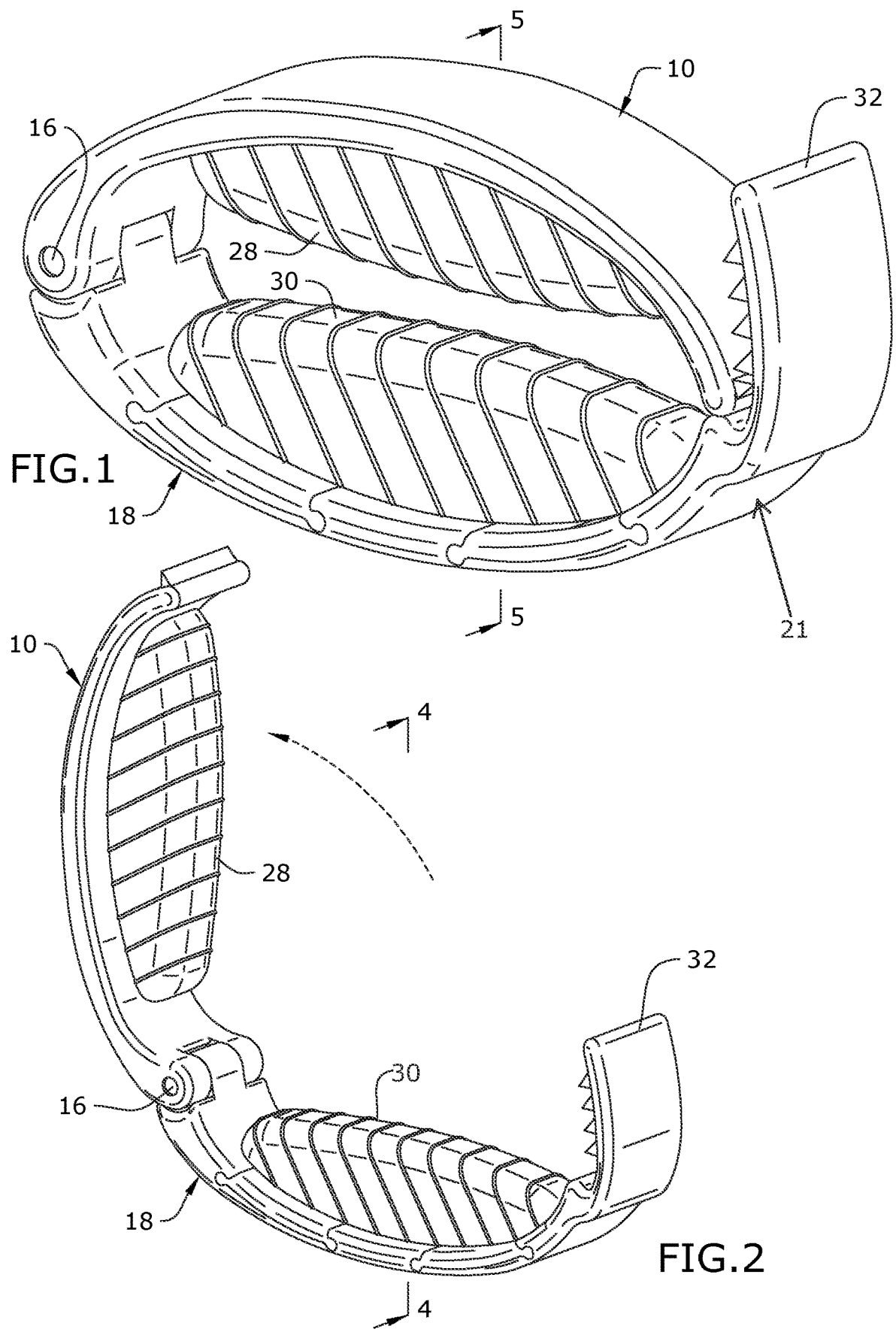

EXTERNAL MALE INCONTINENCE CLAMP

CROSS-REFERENCE TO RELATED APPLICATION

This application is a continuation of U.S. non-provisional application Ser. No. 15/253,051, filed Aug. 31, 2016, and U.S. non-provisional application Ser. No. 16/810,148, filed Mar. 5, 2020, the contents of which are herein incorporated by reference.

BACKGROUND OF THE INVENTION

The present invention relates to incontinence prevention and, more particularly, to an external male incontinence clamp.

Incontinence is a problem encountered by many men and is more common among geriatrics. While the cause of male incontinence may have a variety of different reasons, the uncontrolled and undesired passage of urine is a significant problem resulting in embarrassment, restriction of activities and depression.

While adult diapers are one solution to the problem, they are bulky, retain the moisture, and are embarrassing and difficult for some aging men to handle. Other incontinence clamps have been developed over the years, but since anatomies is different between individuals, it is difficult to create a good fit between the device and the penis. This causes the devices to be extremely uncomfortable and ineffective.

Most of the incontinence clamps developed use foam pads as the interface material between the device and the skin. This creates irritation and swelling of the skin. When the foam collects urine, it is very difficult to clean, and device smells bad. Some other clamps include Polyvinylsiloxane pads. This material is much better than foam but given the properties of the material, it will release natural oil which acts as lubricant and causes the clamp to slip out of position.

As can be seen, there is a need for an improved male incontinence clamp which retains on the penis during everyday activities, that adapts to the anatomy of the patient, that is easy for older men to use and provides control of incontinence without causing irritation or swelling of the tissue.

SUMMARY OF THE INVENTION

In one aspect of the present invention, an incontinence clamp comprises: an upper clamp arm comprising a first end, a second end, an inner surface and an outer surface; a lower clamp comprising a first end, a second end, an inner surface and an outer surface; a hinge pivotably connecting the first end of the upper clamp arm to the first end of the lower clamp; an upper guide coupled to the inner surface of the upper clamp arm and comprising a curved concave inner surface; a lower guide coupled to the inner surface of the lower clamp and comprising a first side portion, a second side portion and a middle portion disposed in between the first side portion and the second side portion, wherein the middle portion comprises a curved convex portion protruding towards the upper clamp arm; and a connector releasably connecting the second end of the upper clamp arm to the second end of the lower clamp arm.

These and other features, aspects and advantages of the present invention will become better understood with reference to the following drawings, description and claims.

BRIEF DESCRIPTION OF THE DRAWINGS

FIG. 1 is a perspective view of an embodiment of the present invention shown in a closed configuration;

FIG. 2 is a perspective view of an embodiment of the present invention shown in an open configuration;

DETAILED DESCRIPTION OF THE INVENTION

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

The present invention includes an external male incontinence clamp. When the clamp is placed on the penis, the device occludes the urethra while promoting blood circulation. The clamp of the present invention includes guides that adapt the user anatomy in shape and size. The material used is biocompatible, does not cause irritation or swelling, promotes a good perspiration of the skin and does not slip off of the penis.

Figure 3:
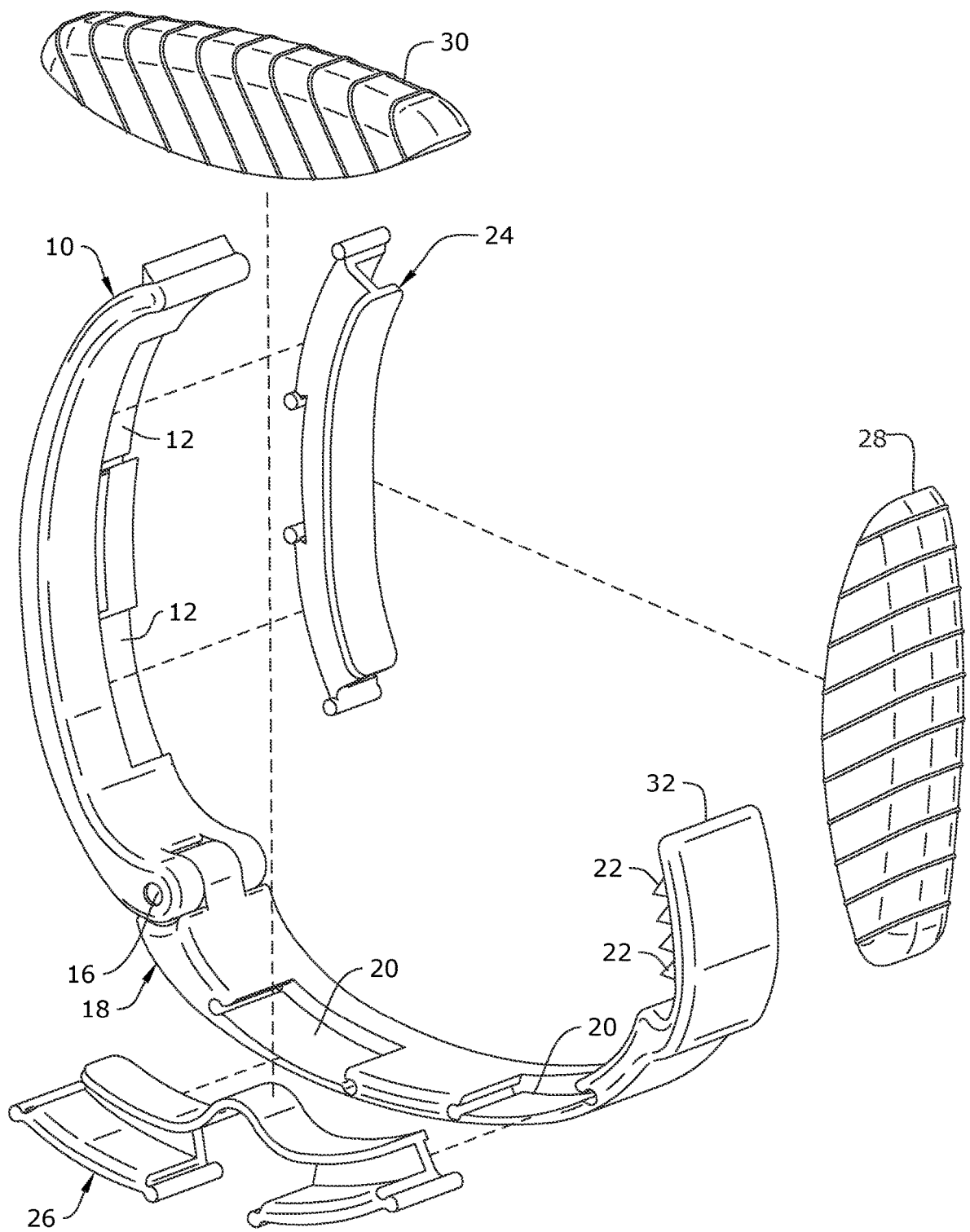
FIG. 3 is an exploded view of an embodiment of the present invention.
Figure 4:
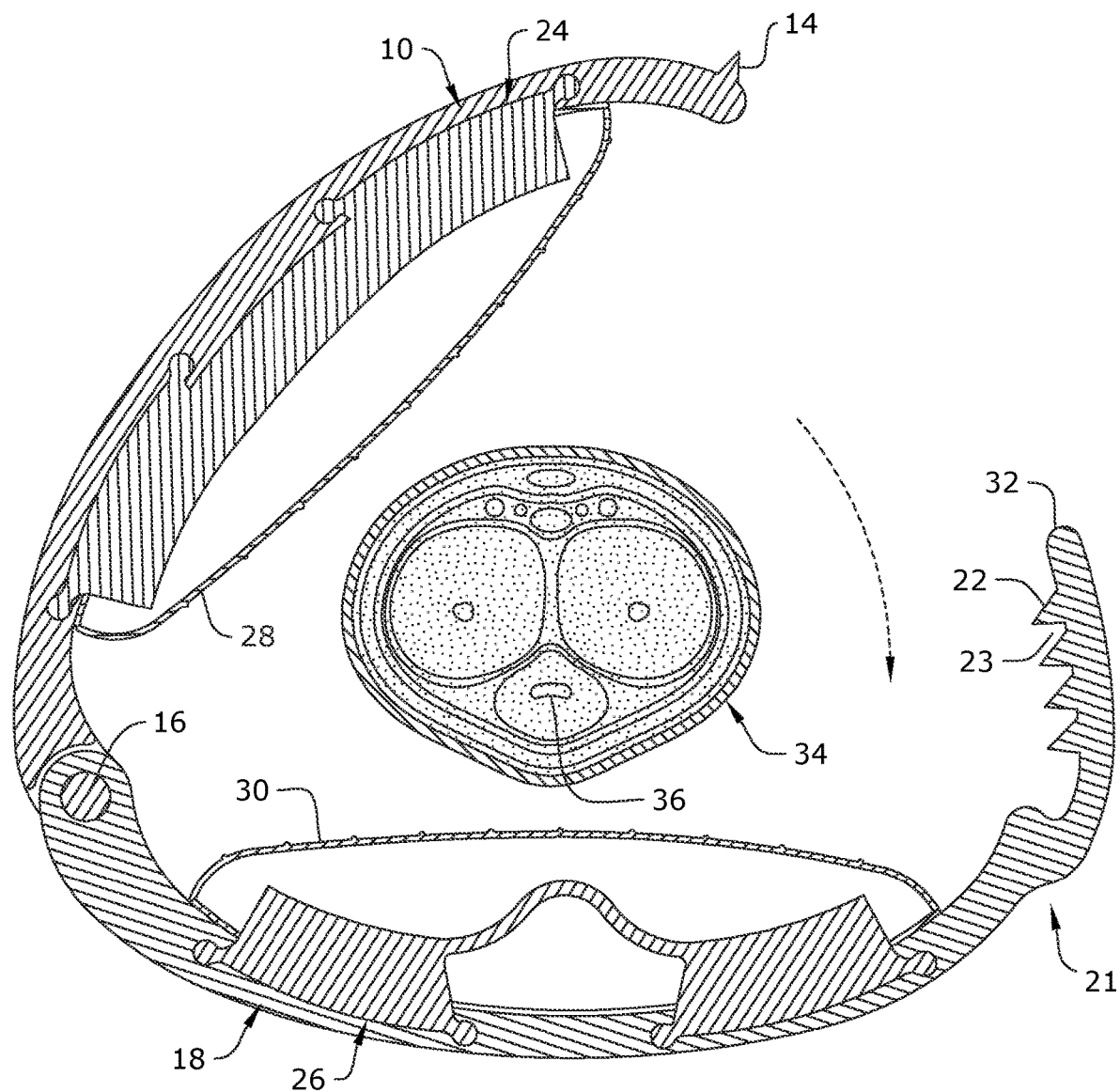
FIG. 4 is a section view of the present invention taken along line 4-4 in FIG. 2.
Figure 5:
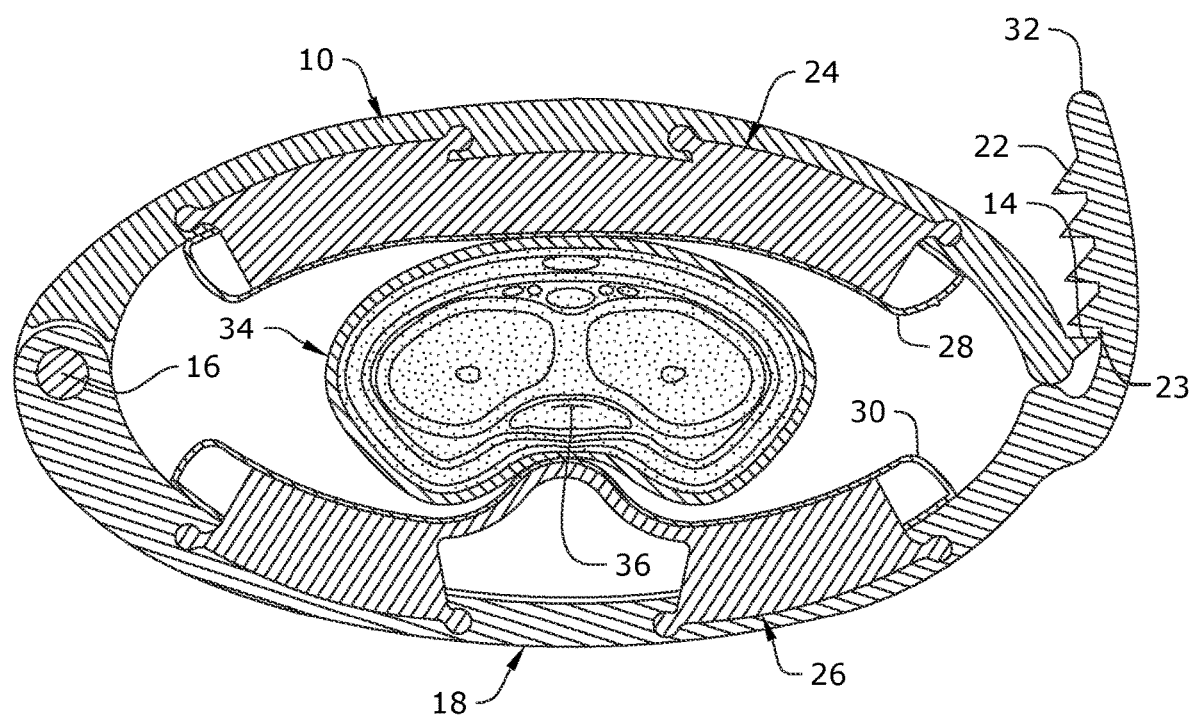
FIG. 5 is a section detail view of the present invention taken along line 5-5 in FIG. 1.

Referring to FIGS. 1 through 5, the present invention includes an incontinence clamp. The incontinence clamp includes an upper clamp arm 10 and a lower clamp arm 18. Each of the upper and lower clamp arms 10, 18 include a first end, a second end, an inner surface and an outer surface. The inner surfaces face each other. A hinge 16 pivotally connects the first ends of the upper and lower clamp arms 10, 18 together. An upper guide 24 is coupled to the inner surface of the upper clamp arm 10 and a lower guide 26 is coupled to the inner surface of the lower clamp arm 18. A connector 21 releasably connects the second ends of the upper clamp arm 10 and the lower clamp arm 18 together.

The upper guide 24 and lower guide 26 contours to the penis 34 and applies pressure to the urethra 36, preventing incontinence. The upper guide 24 includes a curved concave inner surface. The lower guide 26 includes a first side portion, a second side portion and a middle portion disposed in between the first side portion and the second side portion. The middle portion includes a curved convex portion protruding towards the upper clamp arm 10. The first side portion and the second side portion may each include a curved concave inner surface curving in the opposite direction of the middle portion. The upper guide 24 and the lower guide 26 may be formed of a rigid polymer to provide appropriate pressure to the penis 34. For example, the rigid polymer is acrylonitrile butadiene styrene.

In certain embodiments, the upper guide 24 and the lower guide 26 are releasably attached to the inner surface of the upper clamp arm 10 and lower clamp arm 18 respectively. Since the upper and lower guides 24, 26 may be removable, a user may replace the guides 24, 26 depending on the size of the penis 34. In such embodiments, a slot 12 may be formed on the inner surface of the upper clamp arm 10. The upper clamp guide 24 includes a ridge releasably retained within the slot 12. A slot 20 may be formed on the inner surface of the lower clamp arm 18. The lower clamp guide 26 includes a ridge releasably retained within the slot 20.

The present invention may further include a padding 28, 30. An upper padding 28 may be secured to the upper clamp arm 10 and a lower padding 30 may be secured to the lower clamp arm 18. The padding 28, 30 may be in the shape of a cover and is sized to releasably secure over the upper and lower guides 24, 26 respectively. The padding 28, 30 may include ridges formed on an outer surface to prevent slipping. The padding 28, 30 adds comfort to the present invention. The padding 28, 30 may be made of a thermoplastic elastomer.

The connector 21 of the present invention may include a plurality of connecting positions. Each of the connecting positions forms a different internal diameter of the incontinence clamp. For example, one of the second ends includes an interlocking tooth 14 and the other of the second ends includes a plurality of interlocking teeth 22 and a plurality of recesses 23 disposed in a spaced apart relation along a release tab 32. The interlocking tooth 14 is secured in between the plurality of interlocking teeth 22 or engaged with a selected one of the plurality of recesses 23, releasably connecting the second ends together. As illustrated in the Figures, the interlocking tooth 14 may protrude from the outer surface of the upper clamp arm 10. The plurality of interlocking teeth 22 may protrude from an inner surface of a release tab 32 extending from the second end of 10 the lower clamp arm 18. The plurality of recesses 23 are defined along the inner surface of the release tab 32. Pressing the clamp arms 10, 18 together releasably retains the second end of the upper clamp arm 10 to the second end of the lower clamp arm 18. The interlocking tooth 14 disposed in a recess 23 between different interlocking teeth 22 adjusts the diameter of the incontinence clamp. Activation of the release tab 32 disengages the interlocking tooth 14 from its engagement in the corresponding recess 23.

In use, the users select the guides that better correspond to their penis shape and size. Then the user assembles the guides into the clamp by sliding the guides in the slots formed in the inner surface. After assembling the guides, the user assembles the pads over the guides. Once the pads are assembled, the user opens the incontinence clamp by releasing the catch and lifting up the top arm. The user may then place the penis between the pads with the incontinence clamp about halfway down the shaft. Latch the incontinence clamp to compress the urethra at the level that is comfortable to the user. The bottom part of the clamp is designed to concentrate the pressure in the urethra while providing room to the corpora cavernosa to move on the sides. The top part of the clamp is designed to promote a correct blood circulation and sensation, enabling the dorsal arteries, veins, and nerve to be in a pressure significantly lower than the applied in the urethra. Given the variety of guides and pressure levels of the clamp, the adaptation between the device and the penis is much more effective, reliable and healthier for the patient. The pads with ridges permit the correct skin perspiration and prevent slippage. Due to the flexibility of the material, the pads provide comfort to the user.

It should be understood, of course, that the foregoing relates to exemplary embodiments of the invention and that modifications may be made without departing from the spirit and scope of the invention as set forth in the following claims.

What is claimed is:

1. An incontinence clamp comprising:
    an upper clamp arm comprising a first end, a second end, an inner surface, and an outer surface, wherein the upper clamp arm comprises an arcuate inner surface;
    a lower clamp arm comprising a first end, a second end, an inner surface, and an outer surface, wherein the lower clamp arm comprises an arcuate inner surface;
    a hinge pivotably connecting the first end of the upper clamp arm to the first end of the lower clamp arm;
    a removable upper guide spans a majority of the inner surface of the upper clamp arm, the removable upper guide comprising a curved concave-inner surface, and an upper padding releasably secured over a majority of the removable upper guide;
    a removable lower guide spans a majority of the inner surface of the lower clamp arm, the removable lower guide comprising a first side portion, a second side portion and a middle portion disposed in between the first side portion and the second side portion, wherein the middle portion comprises a curved convex portion protruding towards the upper clamp arm, and a lower padding releasably secured over a majority of the removable lower guide;
    wherein at least one of the removable upper guide and the removable lower guide is dimensioned to selectively adjust a size of the incontinence clamp to a user's penis; and
    a connector releasably connecting the second end of the upper clamp arm to the second end of the lower clamp arm.

2. The incontinence clamp of claim 1, wherein the connector comprises a plurality of connecting positions, wherein each of the plurality of connecting positions forms a different internal diameter of the incontinence clamp.

3. The incontinence clamp of claim 2, wherein one of the second end of the upper clamp arm and the lower clamp comprises an interlocking tooth and another of the second end of the upper clamp arm and the lower clamp arm comprises a plurality of recesses engageable by the interlocking tooth, wherein the interlocking tooth is adjustably secured in a selected one the plurality of recesses, releasably connecting the second end of the upper clamp arm and the lower clamp arm together.

4. The incontinence clamp of claim 3, wherein one of the interlocking tooth and the plurality of recesses are carried by a release tab formed as an arcuate extension of the one of the second end of the upper clamp arm and the lower clamp arm, wherein a flexing actuation of the release tab away from the one of the second end of the upper clamp arm and the lower clamp arm of the incontinence clamp releases the interlocking tooth from the plurality of recesses of the incontinence clamp.

5. The incontinence clamp of claim 1, wherein the removable upper guide and the removable lower guide are formed of a rigid polymer.

6. The incontinence clamp of claim 5, wherein the rigid polymer is acrylonitrile butadiene styrene.

7. The incontinence clamp of claim 1, wherein the upper padding and the lower padding are formed of a thermoplastic elastomer.

8. The incontinence clamp of claim 1, wherein the upper padding and the lower padding each comprise a plurality of ridges formed on an outer surface.

9. The incontinence clamp of claim 1, wherein the first side portion and the second side portion comprise a curved concave inner surface.

10. An incontinence clamp comprising:
an upper clamp arm comprising a first end, a second end, an inner surface, and an outer surface, wherein the upper clamp arm comprises an arcuate inner surface;
a lower clamp arm comprising a first end, a second end, an inner surface, and an outer surface, wherein the lower clamp arm comprises an arcuate inner surface;
a hinge pivotably connecting the first end of the upper clamp arm to the first end of the lower clamp arm;
a removable upper guide underlies a majority of the inner surface of the upper clamp arm, the removable upper guide comprising a concave-inner face, and an upper padding releasably secured over a majority of the removable upper guide;
a removable lower guide overlies a majority of the inner surface of the lower clamp arm, the removable lower guide comprising a first side portion, a second side portion and a middle portion disposed in between the first side portion and the second side portion, wherein the middle portion comprises a curved convex portion protruding towards the upper clamp arm, and a lower padding releasably secured over a majority of the removable lower guide; and
a connector releasably connecting the second end of the upper clamp arm to the second end of the lower clamp arm, the connector comprising a release tab integrally formed with and extending from the second end of the lower clamp arm, a plurality of recesses vertically disposed in a spaced apart relation along an inner face of the release tab, an engagement tooth defined on the second end of the upper clamp arm, the engagement tooth configured to cooperatively engage with a selected one of the plurality of recesses, wherein each of the plurality of recesses forms a different internal diameter of the incontinence clamp when the engagement tooth is received within a selected recess.

11. The incontinence clamp of claim 10, wherein the removable upper guide and the removable lower guide are formed of a rigid polymer.

12. The incontinence clamp of claim 11, wherein the rigid polymer is acrylonitrile butadiene styrene.

13. The incontinence clamp of claim 10, wherein at least one of the removable upper guide and the removable lower guide is dimensioned to selectively adjust a size of the incontinence clamp to a user's penis.

14. The incontinence clamp of claim 10, wherein the upper padding and the lower padding are formed of a thermoplastic elastomer.

15. The incontinence clamp of claim 10, wherein the upper padding and the lower padding each comprise a plurality of ridges formed on an outer surface.

16. The incontinence clamp of claim 10, wherein the first side portion and the second side portion comprise a curved concave inner surface.

* * * * *